(12) United States Patent
Liu et al.

(10) Patent No.: US 10,156,518 B2
(45) Date of Patent: Dec. 18, 2018

(54) IMAGE ANALYSIS APPARATUS, IMAGING SYSTEM, SURGERY SUPPORT SYSTEM, IMAGE ANALYSIS METHOD, AND STORAGE MEDIUM

(71) Applicant: NIKON CORPORATION, Minato-ku, Tokyo (JP)

(72) Inventors: Zhen Liu, Tokyo (JP); Takeshi Hataguchi, Tokyo (JP); Hiroki Ishikawa, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/386,254

(22) Filed: Dec. 21, 2016

(65) Prior Publication Data

US 2017/0199120 A1 Jul. 13, 2017

Related U.S. Application Data

(63) Continuation of application No. PCT/JP2015/068021, filed on Jun. 23, 2015.

(30) Foreign Application Priority Data

Jun. 24, 2014 (JP) .................................. 2014-128946

(51) Int. Cl.
*G01J 5/02* (2006.01)
*G01N 21/359* (2014.01)
(Continued)

(52) U.S. Cl.
CPC ........... *G01N 21/359* (2013.01); *A61B 90/00* (2016.02); *A61B 90/361* (2016.02); *A61B 90/37* (2016.02);
(Continued)

(58) Field of Classification Search
CPC . A61B 5/0261; A61B 2090/373; A61B 90/00; A61B 90/30; A61B 90/50;
(Continued)

(56) References Cited

U.S. PATENT DOCUMENTS 8,462,981 B2 * 6/2013 Determan ............ G06K 9/0014
250/339.01
9,274,046 B2 * 3/2016 Stewart ..................... G01J 3/02
(Continued)

FOREIGN PATENT DOCUMENTS

JP    2006-102360 A    4/2006
JP    2007-075366 A    3/2007
(Continued)

OTHER PUBLICATIONS

Author: Hamed Akbar et al.; Title: Cancer detection using infrared hyperspectral imaging, Date: Feb. 2011, Publisher: Currer science.*
(Continued)

*Primary Examiner* — Taeho Jo
(74) *Attorney, Agent, or Firm* — Foley & Lardner LLP

(57) ABSTRACT

An image analysis apparatus includes: a calculator that generates, on the basis of a plurality of sample images obtained by irradiating a biological tissue with light having N wavelength bands selected from a wavelength bandwidth from 950 nm or more to 1600 nm or less as a predetermined wavelength bandwidth, sample data on the tissue in the predetermined wavelength bandwidth; and a data generator that compares the sample data with training data on a substance that is a training target, to generate distribution data indicating a distribution of the substance in the tissue.

16 Claims, 16 Drawing Sheets

(51) Int. Cl.
  *G01N 21/27* (2006.01)
  *G01N 21/3554* (2014.01)
  *A61B 90/00* (2016.01)
(52) U.S. Cl.
  CPC ......... *G01N 21/27* (2013.01); *G01N 21/3554* (2013.01); *A61B 2090/373* (2016.02)
(58) Field of Classification Search
  CPC ............... G01N 21/27; G01N 2201/12; G01N 15/1475; G01N 21/359; G01N 2015/0065; G01N 2021/3595; G01N 2021/6419; G01N 21/314; G01N 21/35
  USPC .................................................. 250/339.06
  See application file for complete search history.

(56) References Cited

U.S. PATENT DOCUMENTS

| | | | | |
|---|---|---|---|---|
| 2003/0153825 | A1* | 8/2003 | Mooradian | A61B 5/0059 600/407 |
| 2005/0196037 | A1* | 9/2005 | Muenzenmayer | G06K 9/3233 382/159 |
| 2005/0270528 | A1* | 12/2005 | Geshwind | G01J 3/02 356/330 |
| 2007/0027362 | A1* | 2/2007 | Handa | A61B 1/00009 600/160 |
| 2007/0152154 | A1* | 7/2007 | DeCamp | G01J 3/2803 250/339.07 |
| 2009/0069653 | A1 | 3/2009 | Yoshida et al. | |
| 2009/0247847 | A1* | 10/2009 | Pogue | A61B 5/0073 600/323 |
| 2010/0069758 | A1* | 3/2010 | Barnes | A61B 5/0059 600/473 |
| 2010/0280762 | A1* | 11/2010 | Maier | A61B 5/417 702/19 |
| 2011/0249911 | A1* | 10/2011 | Determan | G06K 9/0014 382/282 |
| 2012/0310538 | A1* | 12/2012 | Stewart | G06K 9/00127 702/19 |
| 2013/0071002 | A1* | 3/2013 | Otsuka | G06T 7/0012 382/133 |
| 2013/0131517 | A1* | 5/2013 | Panasyuk | A61B 5/0059 600/473 |
| 2013/0178735 | A1* | 7/2013 | Iddan | A61B 5/0066 600/425 |
| 2013/0307950 | A1* | 11/2013 | Aharon | A61B 5/0077 348/65 |
| 2014/0092288 | A1* | 4/2014 | Hattery | A61B 5/0059 348/302 |
| 2014/0093147 | A1* | 4/2014 | Stewart | G01J 3/02 382/128 |
| 2014/0112559 | A1* | 4/2014 | Freeman | A61B 5/0059 382/128 |
| 2014/0168660 | A1* | 6/2014 | Yan | G01B 9/02064 356/511 |
| 2015/0018690 | A1* | 1/2015 | Kang | A61B 5/418 600/473 |
| 2015/0054979 | A1* | 2/2015 | Ou | G02B 21/084 348/222.1 |
| 2016/0091707 | A1 | 3/2016 | Okuno et al. | |

FOREIGN PATENT DOCUMENTS

| | | |
|---|---|---|
| JP | 2007-075445 A | 3/2007 |
| JP | 2009-512500 A | 3/2009 |
| JP | 2009-068940 A | 4/2009 |
| JP | 2010-112926 A | 5/2010 |
| JP | 2011-083486 A | 4/2011 |
| JP | 2013-101109 A | 5/2013 |
| JP | 2014-236911 A | 12/2014 |
| WO | WO-2007/046983 A2 | 4/2007 |

OTHER PUBLICATIONS

Author: Ryo Nagao et al.; Title: Quantitative evaluation of atherosclerotic plaque phantom by near-infrared multispectral imaging with three wavelengths, Date: Mar. 2014, Publisher: SPIE.*
Author: Katsunori Ishii et al.; Title: Near-infrared hyperspectral imaging of atherosclerotic plaque in WHHLMI rabbit artery, Date: 2013, Publisher: SPIE.*
Katsunori Ishii et al., "Method for Diagnosing Arteriosclerosis Using Near Infared Hyperspectral Imaging", Optical Alliance, Sep. 1, 2013, vol. 24, No. 9, pp. 15-19.
Nagao Ryo et al., "Quantitative Evaluation of Atherosclerotic Plaque Phantom by Near-infared Multispectral Imaging with Three Wavelengths", Proceedings of SPIE, Feb. 2014, vol. 8926, pp. 89262V.1-8926V.6.
Japanese Office Action dated Oct. 9, 2018 as issued in corresponding Japanese Application No. 2016-529596 and its English translation thereof.

* cited by examiner $$\alpha = \cos^{-1}\left\{\frac{\sum_{i=1}^{nb} t_i r_i}{\left(\sum_{i=1}^{nb} r_i^2\right)^{1/2} \left(\sum_{i=1}^{nb} t_i^2\right)^{1/2}}\right\}$$

$\cdots$ EXPRESSION(1)

$$d_{ij} = \sqrt{\sum_{k=1}^{p}(x_{ik} - x_{jk})^2} \quad \cdots \text{EXPRESSION (2)}$$

IMAGE ANALYSIS APPARATUS, IMAGING SYSTEM, SURGERY SUPPORT SYSTEM, IMAGE ANALYSIS METHOD, AND STORAGE MEDIUM

CROSS REFERENCE TO RELATED APPLICATION

This is a Continuation of PCT Application No. PCT/JP2015/068021, filed on Jun. 23, 2015. The contents of the above-mentioned application are incorporated herein by reference.

FIELD OF THE INVENTION

The present invention relates to an image analysis apparatus, an imaging system, a surgery support system, an image analysis method, and a storage medium.

BACKGROUND

In medical and other fields, a technology of capturing an image of a biological tissue and utilizing the image for various kinds of diagnosis, tests, and observation is proposed (see, for example, Patent Literature 1). The apparatus according to Patent Literature 1 irradiates a body tissue with infrared rays and acquires an image of subcutaneous vessels on the basis of the infrared rays reflected by the body tissue.

CITATION LIST

Patent Literature

[Patent Literature 1] Japanese Unexamined Patent Application Publication No. 2006-102360

In the above-described technology, information on a tissue cannot be accurately obtained in some cases depending on the wavelength of a light beam detected among light beams radiated from the tissue. The present invention has been made in view of the above-described circumstances, and it is an object thereof to provide an image analysis apparatus, an imaging system, an image analysis method, and a storage medium that are capable of accurately analyzing a distribution of a substance in a biological tissue.

SUMMARY

A first aspect of the present invention provides an image analysis apparatus including: a calculator that generates, on the basis of a plurality of sample images obtained by irradiating a biological tissue with light having N wavelength bands selected from a wavelength bandwidth from 950 nm or more to 1600 nm or less as a predetermined wavelength bandwidth, sample data on the tissue in the predetermined wavelength bandwidth; and a data generator that compares the sample data with training data on a substance that is a training target, to generate distribution data indicating a distribution of the substance in the tissue.

A second aspect of the present invention provides an imaging system including: the image analysis apparatus in the first aspect; and an imaging device that acquires the sample images in the tissue.

A third aspect of the present invention provides an image analysis apparatus including: a calculator that generates, on the basis of a plurality of pieces of sample information obtained by irradiating a biological tissue with infrared light having N wavelength bands selected from a predetermined wavelength bandwidth, sample data on the tissue in the predetermined wavelength bandwidth; and a data generator that compares the sample data with training data on a substance that is a training target, to generate distribution data indicating a distribution of the substance in the tissue, wherein the predetermined wavelength bandwidth is set from a wavelength bandwidth from 700 nm or more to 2500 nm or less as a training region for the training target A fourth aspect of the present invention provides an imaging system including: the image analysis apparatus in the third aspect; and an imaging device that acquires the pieces of sample information in the tissue.

A fifth aspect of the present invention provides a surgery support system including: the imaging system in the second aspect; and an operation device that is capable of treating the tissue.

A sixth aspect of the present invention provides a surgery support system including: the imaging system in the fourth aspect; and an operation device that is capable of treating the tissue.

A seventh aspect of the present invention provides an image analysis method including: generating, on the basis of a plurality of sample images obtained by irradiating a biological tissue with light having N wavelength bands selected from a wavelength bandwidth from 950 nm or more to 1600 nm or less as a predetermined wavelength bandwidth, sample data on the tissue in the predetermined wavelength bandwidth; and comparing the sample data with training data on a substance that is a training target, to generate distribution data indicating a distribution of the substance in the tissue.

An eighth aspect of the present invention provides an image analysis method including: generating, on the basis of a plurality of pieces of sample information obtained by irradiating a biological tissue with infrared light having N wavelength bands selected from a predetermined wavelength bandwidth, sample data on the tissue in the predetermined wavelength bandwidth; and comparing the sample data with training data on a substance that is a training target, to generate distribution data indicating a distribution of the substance in the tissue, wherein the predetermined wavelength bandwidth is set from a wavelength bandwidth from 700 nm or more to 2500 nm or less as a training region for the training target.

A ninth aspect of the present invention provides a storage medium that stores therein an image analysis program that causes a computer to execute: generating, on the basis of a plurality of sample images obtained by irradiating a biological tissue with light having N wavelength bands selected from a wavelength bandwidth from 950 nm or more to 1600 nm or less as a predetermined wavelength bandwidth, sample data on the tissue in the predetermined wavelength bandwidth; and comparing the sample data with training data on a substance that is a training target, to generate distribution data indicating a distribution of the substance in the tissue.

A tenth aspect of the present invention provides a storage medium that stores therein an image analysis program that causes a computer to execute: generating, on the basis of a plurality of pieces of sample information obtained by irradiating a biological tissue with infrared light having N wavelength bands selected from a predetermined wavelength bandwidth, sample data on the tissue in the predetermined wavelength bandwidth; and comparing the sample data with training data on a substance that is a training target, to generate distribution data indicating a distribution of the substance in the tissue, wherein the predetermined wavelength bandwidth is set from a wavelength bandwidth from 700 nm or more to 2500 nm or less as a training region for the training target.

A eleventh aspect of the present invention provides an imaging system including: an imaging device that acquires a hyperspectral image obtained by irradiating a biological tissue with infrared light having a predetermined wavelength band; a calculator that generates, on the basis of the hyperspectral image, sample data on the tissue in the predetermined wavelength band; and a data generator that compares the sample data with training data on water that is a training target, to generate first image data indicating a distribution of the water in the tissue, and compares the sample data with training data on lipid that is a training target, to generate second image data indicating a distribution of the lipid in the tissue.

A twelfth aspect of the present invention provides a surgery support system including: the imaging system in the eleventh aspect; and a DISPLAY that displays an image based on the first image data or an image based on the second image data.

DETAILED DESCRIPTION OF EMBODIMENTS

Figure 1:
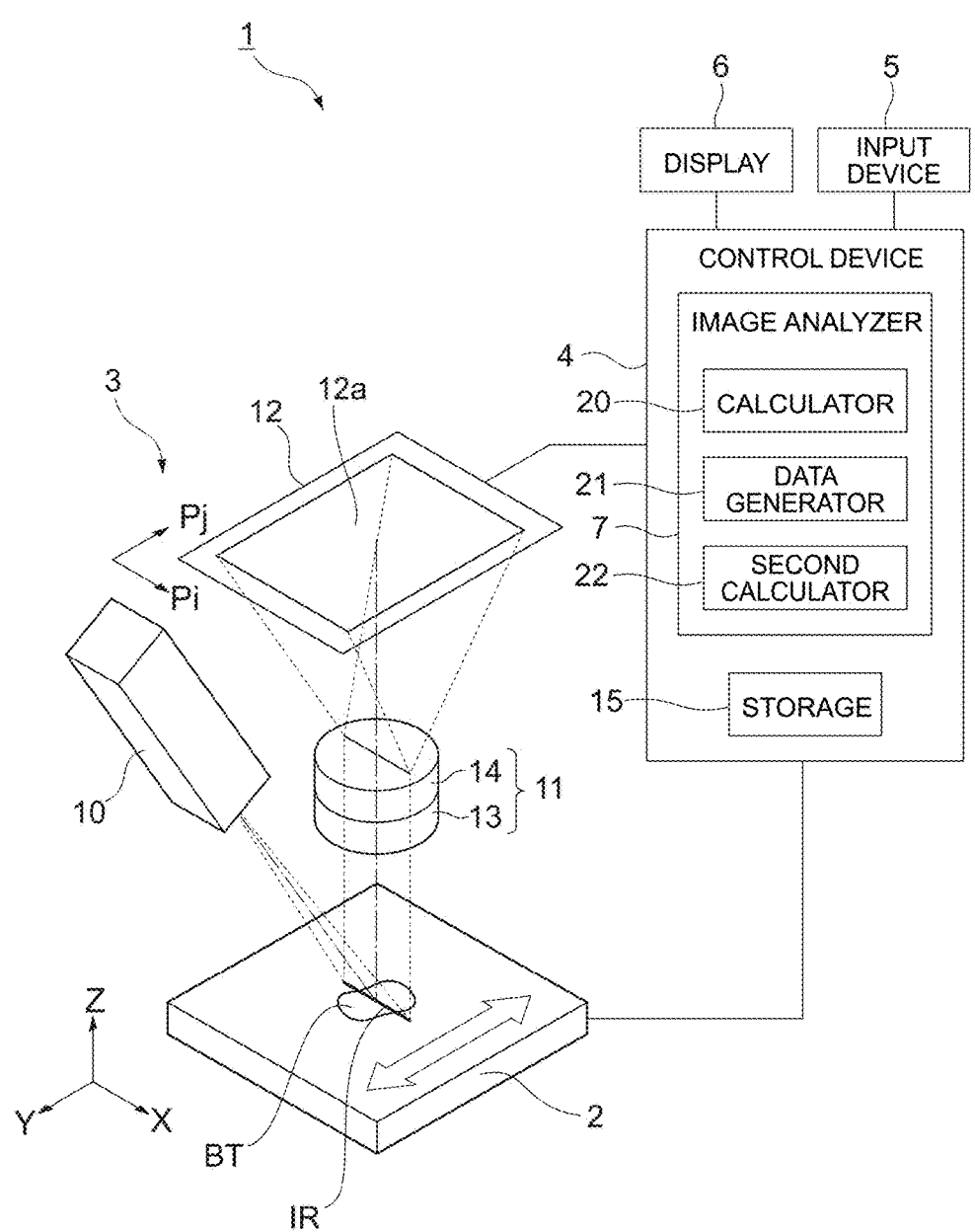
FIG. 1 is a diagram showing an imaging system according to the present embodiment.

FIG. 1 is a diagram showing an imaging system 1 according to the present embodiment. For example, the imaging system 1 is used for pathological anatomy, pathological diagnosis, and biopsy for a biological tissue BT, a biological operation (for example, a surgical operation), and other purposes. The imaging system 1 can be applied to medical applications, test applications, and examination applications, including procedures involving an incision of a tissue BT, such as a general operation, and various kinds of tests involving no incision of a tissue BT.

A tissue BT is, for example, a tissue of a human, or may be a tissue of a living organism (for example, an animal) other than a human. The tissue BT may be a tissue cut away from a living organism, or may be a tissue attached to a living organism. The tissue BT may be a tissue (biological tissue) of a living organism (living body), or may be a tissue of a dead organism (dead body). The tissue BT may be an object excised from a living organism. For example, the tissue BT may include any organ of a living organism, may include a skin, and may include a viscus, which is on the inner side of the skin.

The imaging system 1 includes a stage device 2, an imaging apparatus (imaging device) 3, a control device 4, an input device 5, and a DISPLAY (display) 6. The imaging system 1 operates as follows, for example. A tissue BT can be disposed on the top surface of the stage device 2. The imaging apparatus 3 captures an image of a biological tissue BT disposed on the stage device 2. The control device 4 controls each part in the imaging system 1 on the basis of control signals of instructions and settings input to the input device 5 from an operator (user). An image analyzer 7 is embedded in the control device 4. The image analyzer (image analysis apparatus) 7 generates distribution data indicating a distribution of substances in the tissue ET by using a plurality of sample images in which the tissue BT is imaged. The control device 4 displays various kinds of information on the DISPLAY 6. For example, the control device 4 uses the distribution data generated by the image analyzer 7 to display an image indicating a distribution of substances in the tissue ET on the DISPLAY 6. For example, the image analyzer 7 in the present embodiment can generate distribution data by using a method of collating sample data and training data to be described later. Each part in the imaging system 1, a method of generating distribution data, and the like will be described below.

The imaging apparatus 3 includes a sensor (light detector 12) that can acquire a plurality of pieces of spectrum data at one pixel in an image by single photographing as represented by a hyperspectral camera. The imaging apparatus 3 acquires a hyperspectral image as a plurality of sample images in a biological tissue BT in a predetermined wavelength bandwidth. Thus, the imaging apparatus 3 can acquire a plurality of pieces of spectrum data for each pixel in the sample image. The imaging apparatus 3 includes a light source 10, an imaging optical system 11, and the light detector 12.

The light source 10 includes, for example, a halogen lamp or an infrared LED (infrared light emitting diode). The light source 10 outputs infrared light in a wavelength band used for image analysis by the image analyzer 7. The wavelength band used for image analysis is, for example, at least a part of a wavelength bandwidth from 950 nm or more to 1600 nm or less. Accordingly, the light source 10 in the imaging apparatus 3 can radiate light having a wavelength bandwidth including at least a part of a wavelength bandwidth from 950 nm or more to 1600 nm or less.

The light source 10 illuminates a lighting region IR on the stage device 2 with infrared light. The lighting region IR is set as a linear shape elongated in one direction. In the present embodiment, for example, the light source 10 outputs infrared light having a spot shape elongated in one direction.

Referring to an XYZ orthogonal coordinate system shown in FIG. 1, the positional relation among elements and the like will be described below. In the XYZ orthogonal coordinate system, the longitudinal direction of the lighting region IR is referred to as X-axis direction, and the direction orthogonal to the X-axis direction on the stage device 2 is referred to as Y-axis direction. The direction orthogonal to each of the X-axis direction and the Y-axis direction is referred to as Z-axis direction. The X-axis direction and the Y-axis direction are set to the horizontal direction, for example, and the Z-axis direction is set to the vertical direction, for example.

The imaging optical system 11 guides light radiated from the lighting region IR (tissue BT) on the stage device 2 to the light detector 12. The imaging optical system 11 includes a lens 13 and a spectrometer 14. The lens 13 condenses the light radiated from the tissue BT onto the light detector 12. The spectrometer 14 includes, for example, a prism or a diffraction grating, a slit, or the like, and disperses the light radiated from the tissue BT into components in a plurality of wavelength bands. The spectrometer 14 disperses light radiated from each point on the tissue BT into spectral light having a spot shape elongated in the Y-axis direction. For example, the spectrometer 14 disperses short-wavelength components in the spectral light to one side in the Y-axis direction, and disperses long-wavelength components in the spectral light to the other side in the Y-axis direction.

The light detector 12 includes a two-dimensional image sensor, such as a CMOS sensor or a CCD sensor. The light detector 12 has a light receiving surface 12a on which photoelectric conversion elements such as photodiodes are arranged. On the light receiving surface 12a, a region where one photodiode is disposed corresponds to one pixel. In the following description, on the light receiving surface 12a, the direction corresponding to the longitudinal direction of the lighting region IR is referred to as Pi direction, and the direction orthogonal to the Pi direction is referred to as Pj direction. The Pi direction is a vertical scanning direction, for example, and the Pj direction is a horizontal scanning direction, for example. Pixels in the light detector 12 are arranged in each of the Pi direction and the Pj direction. The light detector 12 has such similar functions as to those of the above-described hyperspectral camera.

Attention is now focused on a plurality of pixels arranged in the Pj direction (horizontal scanning line). The spectrometer 14 disperses light radiated from each point on the tissue BT into spectral light that distributes in the direction orthogonal to the longitudinal direction of the lighting region IR. Accordingly, a short-wavelength component in the spectral light enters a pixel disposed on one end side in the horizontal scanning line, and a long-wavelength component in the spectral light enters a pixel disposed on the other end side in the horizontal scanning line. In this manner, the light detector 12 can detect light radiated from a part on the tissue BT separately for each wavelength band by using the plurality of pixels arranged on the horizontal scanning line. For example, the light source 10 outputs infrared light over a broad wavelength bandwidth, and each of the pixels in the light detector 12 each detect light having a wavelength band narrower than that of the infrared light output from the light source 10.

For example, the wavelength of light entering a pixel disposed on one end in the horizontal scanning line is represented by $\lambda 1$, and the wavelength of light entering a pixel on the other end in the horizontal scanning line is represented by $\lambda 2$. When the number of pixels arranged on the horizontal scanning line is N, the light detector 12 can detect light having a wavelength bandwidth from the wavelength $\lambda 1$ to the wavelength $\lambda 2$ separately for each of the N wavelength bands. The wavelength width of the N wavelength bands depends on $\lambda 1$, $\lambda 2$, and N. For example, when the number of pixels in the horizontal scanning direction is 1280, the wavelength width can be set to about several nm.

The light detector 12 captures an image of a linear part of the tissue BT that is disposed in the lighting region IR by single imaging processing. In the present embodiment, the stage device 2 is movable in a predetermined direction while holding the tissue BT, so that the relative positions between the lighting region IR and the tissue BT can be changed. When the stage device 2 moves in the Y-axis direction while holding the tissue BT, the relative positions between the lighting region IR and the tissue BT change in the Y-axis direction, and the tissue BT is scanned with light from the light source 10. The control device 4 controls the imaging apparatus 3 to repeatedly execute imaging processing while moving the stage device 2 holding the tissue BT in the Y-axis direction, thereby acquiring a two-dimensional image of the tissue BT.

The control device 4 includes an image analyzer 7 and a STORAGE 15. The image analyzer 7 uses a hyperspectral image (a plurality of sample images) captured by the imaging apparatus 3 to analyze optical properties (for example, spectral properties) of the biological tissue BT. In the present embodiment, the control device 4 stores various kinds of information, such as sample images acquired from the imaging apparatus 3, in the STORAGE 15. The image analyzer 7 reads various kinds of information from the STORAGE 15 and processes the information. The image analyzer 7 includes a calculator 20, a data generator 21, and a second calculator 22.

On the basis of a plurality of sample images, the calculator 20 generates sample data based on optical properties of the tissue BT in a predetermined wavelength bandwidth. For example, the predetermined wavelength bandwidth is set within a wavelength bandwidth from 950 nm or more to 1600 nm or less. The plurality of sample images are images that are obtained by sequentially or concurrently irradiating the biological tissue BT with light having N wavelength bands (N is an integer of 2 or more) selected from the predetermined wavelength bandwidth. The plurality of sample images are obtained from the capture result (detection result) of the imaging apparatus 3. In the present embodiment, the predetermined wavelength bandwidth used to obtain a plurality of sample images is the same as a wavelength bandwidth in a training region described later. Light radiated from the tissue BT includes light reflected by or transmitted through the tissue BT when the tissue BT is irradiated with light and light (for example, fluorescence or phosphorescence) emitted from the tissue BT when the tissue BT is irradiated with light.

Figure 2A:
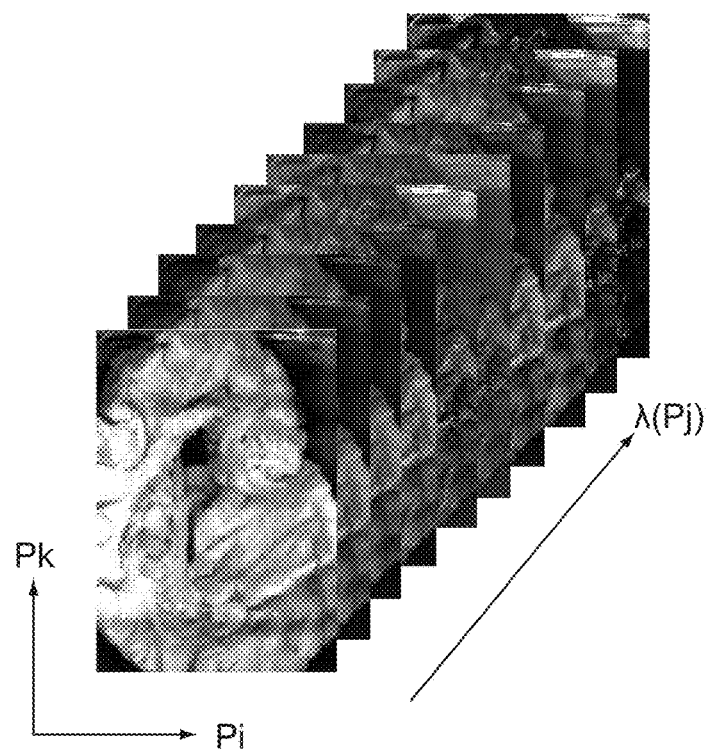
FIGS. 2A and 2B are each a diagram for describing sample data according to the present embodiment.
Figure 2B:
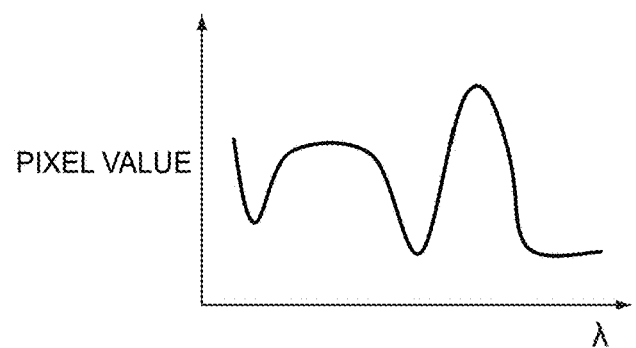

FIGS. 2A and 2B are each a diagram for describing sample data generated by the calculator 20. FIG. 2A shows a conceptual diagram of cube data obtained from the capture result of the imaging apparatus 3, and FIG. 2B shows a conceptual diagram of a pixel value with respect to each wavelength at one pixel in a sample image.

The cube data shown in FIG. 2A has a data structure in which pixel values are arranged corresponding to each of three directions of the Pi direction, the Pk direction, and the $\lambda$ direction. The Pi direction is a direction corresponding to the X-axis direction on the stage device 2. The Pk direction is a direction corresponding to the Y-axis direction on the stage device 2. The $\lambda$ direction is a direction corresponding to the Pj direction on the light receiving surface 12a of the light detector 12. $\lambda$ in the $\lambda$ direction represents a wavelength band.

As described above, the imaging apparatus 3 acquires a sample image in which pixel values are arranged in two directions of the Pi direction and the Pj direction for each imaging processing. The control device 4 acquires the sample image generated by the imaging apparatus 3, and associates the sample image with the position of the stage device 2 in the Y-axis direction. The control device 4 stores each pixel value in the sample image as a pixel value on the Piλ plane at the position in the Pk direction corresponding to the position of the stage device 2 in the Y-axis direction. In this manner, the cube data shown in FIG. 2A is obtained.

In the cube data in FIG. 2A, pixel values on the PiPk plane in a predetermined wavelength band are read to obtain a spatial distribution of light intensity of light having the predetermined wavelength band radiated from the XY place. Pixel values arranged in the λ direction at the same pixel freely selected on the PiPk plane are read to obtain a distribution of pixel values with respect to each wavelength as shown in FIG. 2B (distribution data on pixel values in a sample, an optical spectrum of a sample). Pixel values, which are values for each wavelength band, are a discrete distribution. Discrete values shown in FIG. 2B are connected by a smooth line.

In the present embodiment, the light detector 12 in the imaging apparatus 3 detects light reflected and scattered by the tissue BT. Thus, the distribution of a pixel value with respect to each wavelength depends on the distribution of the reflectance (optical properties value) of a part on the tissue BT corresponding to this single pixel with respect to the wavelength. Accordingly, for example, the sample data is data based on optical properties of the tissue BT in the predetermined wavelength bandwidth. For example, the sample data includes at least one of the above-described cube data (for example, FIG. 2A) or the above-described pixel value distribution data (for example, FIG. 2B) calculated on the basis of the cube data.

The data generator 21 compares the sample data generated by the calculator 20 with training data on a substance (component) as a training target to generate distribution data indicating a distribution of the substance (component) in the tissue BT (substance distribution data, component distribution data). For example, the substance as a training target (hereinafter abbreviated as training substance) is selected from water, lipid, proteins, and bloods. A living body is mainly composed of water and lipid, and hence grasping the balance of water and lipid in a living body by using the method in the present embodiment helps to determine a lesion area in the living body.

For example, when lipid is selected as a training substance, training data includes lipid data based on a distribution of light intensity of light radiated from lipid irradiated with light having a predetermined wavelength bandwidth with respect to the wavelength in the predetermined wavelength bandwidth. In this case, for example, the predetermined wavelength bandwidth is selected from 950 nm or more to 1600 nm or less. For example, when water is selected as a training substance, training data includes water data based on a distribution of light intensity of light radiated from water irradiated with light having a predetermined wavelength bandwidth with respect to the wavelength in the predetermined wavelength bandwidth. When at least one of water, lipid, or bloods (blood vessels) is selected as a training substance, the predetermined wavelength bandwidth is selected from a wavelength bandwidth from 950 nm or more to 1300 nm or less or a wavelength bandwidth from 950 nm or more to 1600 nm or less.

Figure 3:
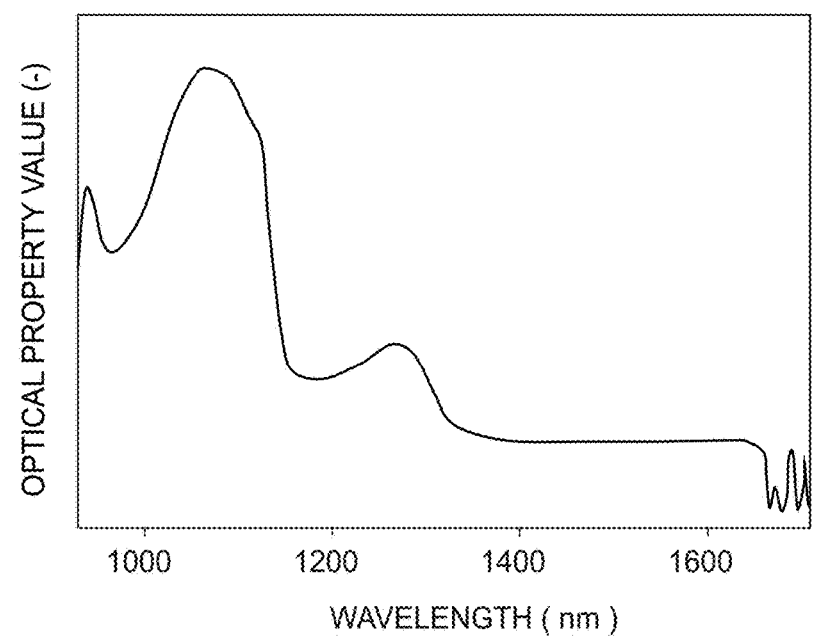
FIG. 3 is a diagram for describing training data according to the present embodiment.

FIG. 3 is a diagram for describing training data. FIG. 3 is data on spectrum properties (optical properties) indicating a distribution (optical spectrum) of light intensity of light radiated from water (training substance) irradiated with light having a predetermined wavelength bandwidth with respect to the wavelength in the predetermined wavelength bandwidth. In the present embodiment, the above-described predetermined wavelength bandwidth is selected on the basis of the optical spectrum (or spectrum properties) of water as shown in FIG. 3, and is set as a training region. For example, the training region is selected from a near-infrared region (for example, 700 nm or more and 2500 nm or less), and is set to 700 nm or more and 2500 nm or less, 800 nm or more and 1000 nm or less, 800 nm or more and 1300 nm or less, 950 nm or more and 1300 nm or less, 1050 nm or more and 1350 nm or less, 1000 nm or more and 1400 nm or less, or 950 nm or more and 1600 nm or less. The training data includes data based on optical properties indicating an optical spectrum of the training substance in the training region in the predetermined wavelength bandwidth. As the training data, data including the same item of optical properties as the sample data is used. In the present embodiment, the sample data is data based on absorption and scattering properties of the tissue BT with respect to the wavelength, and as the training data, data based on absorption and scattering properties of the training substance with respect to the wavelength is used.

Similarly to the above-described sample data, the training data in the present embodiment is generated on the basis of a plurality of training images for respective wavelength bands obtained by concurrently or sequentially irradiating a substance (for example, water or lipid) with light having M wavelength bands (M is an integer of 2 or more) selected from a training region in a predetermined wavelength bandwidth. Thus, the training images in the present embodiment are hyperspectral images similarly to the above-described plurality of sample images. For example, the imaging system 1 arranges a training substance instead of a tissue BT on the stage device 2, and generates training data by using a plurality of training images that are captured by the imaging apparatus 3 while the light source 10 irradiates the training substance with infrared light in a predetermined wavelength bandwidth (training region). For example, the calculator 20 can obtain a distribution of pixel values in M wavelength bands at the same pixel in the training images (distribution data on pixel values in the training substance or an optical spectrum of the training substance). Thus, for example, the training data is data based on spectrum properties of the training substance in the predetermined wavelength bandwidth. For example, the training data includes at least one of cube data on the training substance, such as the sample cube data in FIG. 2A, or the distribution data (for example, distribution data as shown in FIG. 2B) of pixel values calculated on the basis of the cube data. The data generator 21 compares the training data with the above-described sample data to generate distribution data that distinguishes the training substance in the tissue BT. The training data in the present embodiment is prepared in advance before an image of the biological tissue BT is captured, and is stored in the STORAGE 15. The N wavelength bands and the M wavelength bands selected from the predetermined wavelength bandwidth are the same wavelength bands. Thus, the N wavelength bands used for the sample images have the same wavelength bands as the M wavelength bands used for the training images. In this case, N and M, which are the numbers of wavelength bands selected from the predetermined wavelength bandwidth, are equal numbers (N=M).

The data generator 21 calculates an index value indicating similarity (degree of similarity) between the sample data and the training data, and generates the above-described distribution data by using the calculated index value. Examples of the method of calculating the index value indicating the degree of similarity between the sample data and the training data include parallelpiped classification, minimum distance classification, binary encoding classification, Mahalanobis distance classification, maximum likelihood classification, Neural net classification, support vector machine classification, adaptive coherence estimator classification, spectral information divergence classification, orthogonal subspace projection classification, spectral correlation mapper, principal component analysis (PCA), independent component analysis (ICA), and spectral angle mapper classification.

The calculation of the index value in the present embodiment uses the spectral angle mapper classification as one example. In the present embodiment, the data generator uses the spectral angle mapper classification to generate distribution data that distinguishes a training substance in the tissue BT on the basis of sample data and training data.

In the present embodiment, the data generator 21 generates distribution data on the basis of a spectral angle between a vector (sample vector) in an N-dimensional space obtained from sample data and a vector (training vector) in an M-dimensional space obtained from training data. The angle between the two vectors indicates the similarity of spectra, and a smaller angle (spectral angle) indicates a larger similarity. For example, the vector in the N-dimensional space obtained from the sample data is a vector in an N-dimensional spectrum space, which represents a distribution (for example, optical spectrum) of pixel values that are extracted from the same pixels in N sample images in N wavelength bands and arranged in the order of the wavelength bands. For example, the vector in the M-dimensional space obtained from the training data is a vector in an M-dimensional spectrum space, which represents a distribution (for example, optical spectrum) of pixel values that are extracted from the same pixels in M training images in M wavelength bands and arranged in the order of the wavelength bands.

Figures 4A, 4B:
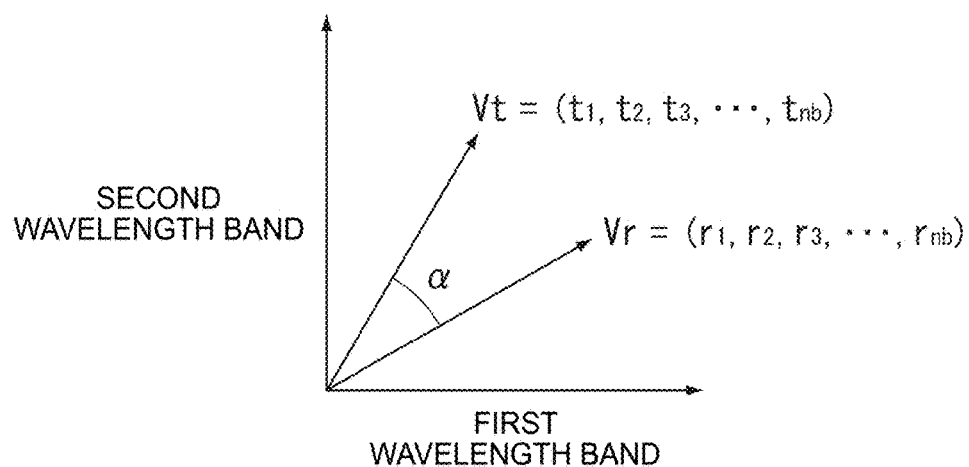
FIGS. 4A and 4B are each a diagram for describing a spectral angle according to the present embodiment.

FIGS. 4A and 4B are each a diagram for describing the above-described spectrum angle. FIG. 4A shows a conceptual diagram of the spectrum angle, and FIG. 4B shows Expression (1) indicating an expression of calculating the spectral angle. In the present embodiment, N=M is established, and N=M=nb is set in FIG. 4A. Focus is paid on one pixel freely selected in a sample image. When pixel values that are included in cube data (see FIG. 2A) as pixel values of the pixel are arranged in ascending or descending order of the wavelength bands, a vector in an N-dimensional space having the same dimension as the number (N) of the wavelength bands is obtained. For example, symbol Vt in FIG. 4A represents a vector in the N-dimensional space obtained from sample data, and is a vector in which N (nb) pixel values are arranged in a manner that a pixel value $t_1$ corresponding to a first wavelength band and a pixel value $t_2$ corresponding to a second wavelength band are arranged. For a training image, a vector Vr in which N (nb) pixel values are arranged in a manner that a pixel value $r_1$ corresponding to the first wavelength band and a pixel value $r_2$ corresponding to the second wavelength band are arranged is similarly obtained.

Each of the vector Vt and the vector Vr is a vector in the N-dimensional space, but FIG. 4A shows projection on a two-dimensional plane of the first wavelength band and the second wavelength band. The vector Vt and the vector Vr may be vectors in the two-dimensional space or may be vectors in three- or higher-dimensional spaces. For example, when a vector in the two-dimensional space is used, the image analyzer 7 in the present embodiment generates the above-described sample data on the basis of a plurality of (in this case, two) sample images obtained by irradiating a tissue BT with light having a first wavelength band and light having a second wavelength band that are specified from a predetermined wavelength bandwidth (training region), and generates distribution data on the basis of the spectral angle between a vector in the two-dimensional space obtained from the sample data and a vector in the two-dimensional space obtained from training data that is obtained similarly to the sample data. In this manner, the image analyzer 7 in the present embodiment can generate distribution data by calculating sample data and training data in at least two wavelength bands (for example, two infrared light beams) specified from a predetermined wavelength bandwidth (for example, training region) with use of the spectral angle mapper classification (or the minimum Euclidean distance classification described later).

The vector Vt represents the optical properties (spectrum properties) shown in FIG. 2B, and the vector Vr represents optical properties corresponding to the vector Vt. Thus, a smaller angle (spectral angle $\alpha$) formed between the vector Vt and the vector Vr indicates that optical properties of a part of the tissue BT represented by the vector Vt are more similar to optical properties of a training substance. $\cos \alpha$ for the spectral angle $\alpha$ is a value obtained by dividing the inner product of the vector Vt and the vector Vr by the magnitude of the vector Vt and the magnitude of the vector Vr. Thus, the spectral angle $\alpha$ is less affected by the difference in average luminance caused by a sensor gain in the light detector 12.

The data generator 21 calculates the spectral angle $\alpha$ for each pixel in an image. The data generator 21 sequentially selects pixels on the PiPk plane in the cube data shown in FIG. 2A, and repeatedly performs the processing of calculating the spectral angle $\alpha$ between sample data and training data at the selected pixels. The data generator 21 arranges (maps) the calculation results for the respective pixels in association with the positions of the pixels, thereby generating distribution data in the image format.

For example, the data generator 21 converts the spectral angle $\alpha$ calculated for each pixel in the sample image into a gray-scale value, and arranges the gray-scale values in accordance with the positions of the pixels, thereby generating bitmap data as distribution data on a training substance (target substance). For example, an image indicated by the bitmap data is a rule image (reference image) in which a pixel having a small spectral angle $\alpha$ is represented by a small gray-scale value (dark display). In the tissue ST on the rule image, a part where the degree of similarity to the training data is high is displayed dark, and a part where the degree of similarity to the training data is low is displayed bright. In this manner, the image analyzer 7 in the present embodiment can perform the processing of combining the captured sample image with the generated rule image to provide an image that can distinguish the training substance in the tissue BT.

The data generator 21 extracts pixels at which the spectral angle $\alpha$ calculated for each pixel in the sample image is a predetermined threshold or less, and generates distribution data indicating a group of pixels at which the spectral angles $\alpha$ are a threshold or less. For example, the data generator 21 binarizes the pixel values in a manner that the gray-scale value of a pixel at which the spectral angle $\alpha$ is a threshold or less is 0 and the gray-scale value of a pixel at which the spectral angle α is large than a threshold is 255. The data generator 21 arranges the thus binarized gray-scale values in accordance with the positions of the pixels, thereby generating data on a binary image (reference image) as distribution data. In the tissue ET on the binary image, a part where the degree of similarity to the training data is high is displayed in black, for example, and a part where the degree of similarity to the training data is low is displayed in white, for example. In this manner, the image analyzer 7 in the present embodiment can perform the processing of combining the captured sample image with the generated binary image to provide an image that can distinguish the training substance in the tissue BT.

The data generator 21 can generate distribution data for each of a plurality of training substances. The data generator 21 stores distribution data for each training substance in the STORAGE 15. For example, the data generator 21 uses training data corresponding to water to generate water distribution data indicating a distribution of water in the tissue BT. The data generator 21 uses training data corresponding to lipid to generate lipid distribution data indicating a distribution of lipid in the tissue BT. The data generator 21 stores the generated water distribution data and the generated lipid distribution data in the STORAGE 15.

Then, the second calculator 22 performs calculation by using the pieces of distribution data generated by the data generator 21. The second calculator 22 reads the distribution data stored in the STORAGE 15 for calculation. For example, the second calculator 22 calculates the difference between the water distribution data and the lipid distribution data. In the present embodiment, the distribution data is in the image format, and the second calculator 22 calculates the difference of pixel values of pixels at the same position in a water image indicated by the water distribution data and a lipid image indicated by the lipid distribution data, and arranges the differential values in accordance with the positions of pixels, thereby generating data on a differential image. In the differential image (reference image), a part where the proportion of lipid is high and the proportion of water is low has a lower gray-scale value. In this manner, when a plurality of training substances are selected, the second calculator 22 can generate an image in which the proportions of the training substances in a sample image are emphasized.

The calculator 20 can display a distribution image indicated by the above-described distribution data as a color image. For example, the calculator 20 can generate image data in which the gray-scale value of a part of a water image where the proportion of water is high is a gray-scale value for green. The calculator 20 can generate image data in which the gray-scale value of a part of a lipid image where the proportion of lipid is high is a gray-scale value for red.

The second calculator 22 can generate a color image in which a part of the above-described differential image where the proportion of water to lipid is large and a part of the above-described differential image where the proportion of lipid to water is large are displayed in different colors. In this manner, the distributions of training substances are displayed in different colors depending on the kind of training substances, and hence the distributions of the training substances can be clearly visually recognized. For example, colors in the reference image are stored in the STORAGE 15 as setting information. The setting information can be changed by using the input device 5.

The second calculator 22 can generate data on an overlay image in which at least one of the distribution image or the differential image is overlaid on the sample image of the tissue BT. For example, the sample image data is obtained by extracting data on the PiPk plane in a freely selected wavelength from the cube data shown in FIG. 2A. The sample image data may be data on a visual image obtained by capturing an image of the tissue BT with a visible light camera. By generating an image in which a reference image such as a distribution image is overlaid on the visible image, it becomes more easily visually recognize which part on the tissue BT a training substance is distributed.

Figure 5:
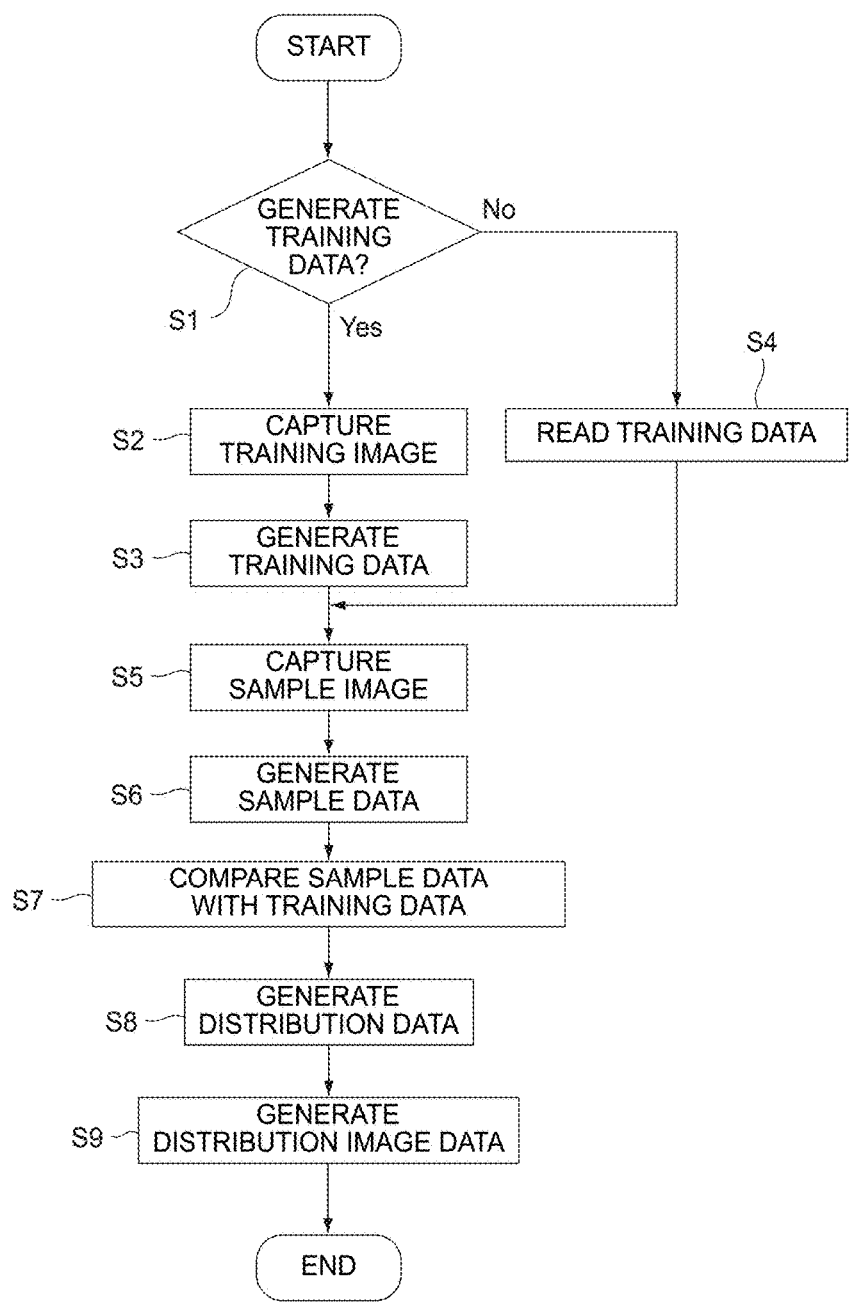
FIG. 5 is a flowchart showing an operation of the imaging system according to the present embodiment.

Next, an image analysis method according to the present embodiment will be described on the basis of the operation of the above-described imaging system 1. FIG. 5 is a flowchart showing an example of the operation of the imaging system 1.

In the present embodiment, first, the control device 4 determines whether to generate training data (Step S1). For example, the control device 4 displays information to ask for an instruction whether to generate training data on the DISPLAY 6 in FIG. 1. Then, the input device 5 receives the instruction whether to generate training data, and transmits a signal of the instruction to the control device 4. When the control device 4 receives a signal indicating an instruction to generate training data (Step S1; Yes), the control device 4 starts a sequence for generating training data (Step S2, Step S3).

Next, in the sequence for generating training data, a training substance is disposed on the stage device 2. At Step S2, the control device 4 controls the light source 10 to irradiate the training substance with infrared light having a predetermined wavelength bandwidth. The control device 4 captures an image of the training substance irradiated with the infrared light while moving the stage device 2 relative to the light source 10. The imaging apparatus 3 detects light radiated from the training substance separately for N wavelength bands. At Step S3, the control device 4 performs statistical processing on pixel values of a plurality of pixels in a training image by which light having the same wavelength band is detected, thereby calculating a representative value of the pixel values for this wavelength band. The control device 4 calculates the representative value for each of the N wavelength bands included in the predetermined wavelength bandwidth, thereby calculating a vector in an N-dimensional space for each pixel as the training data. When the control device 4 receives a signal indicating an instruction not to generate training data at Step S1 (Step S1; No), the control device 4 reads training data stored in the STORAGE 15 in advance from the STORAGE 15 (Step S4). For example, when training data has already been generated and this training data is used, new training data is not generated at Step S1.

After the control device 4 generates training data or acquires training data by reading, the control device 4 starts a sequence for generating sample data (Step S5, Step S6). In the sequence for generating sample data, a biological tissue BT is disposed on the stage device 2. At Step S5, the control device 4 controls the light source 10 to irradiate the tissue BT with infrared light having a predetermined wavelength bandwidth. The control device 4 captures an image of the tissue BT irradiated with the infrared light while moving the stage device 2 relative to the light source 10. The imaging apparatus 3 detects light radiated from each part of the tissue BT separately for N wavelength bands.

At Step S6 after the capture of a plurality of sample images (N sample images) is finished, the calculator 20 in the image analyzer 7 generates sample data. The calculator 20 associates each of the sample images with the position of the stage device 2 in the Y-axis direction at the time when each sample image is captured, thereby generating cube data shown in FIG. 2A as the sample data. The calculator 20 stores the generated cube data in the STORAGE 15.

Figure 6:
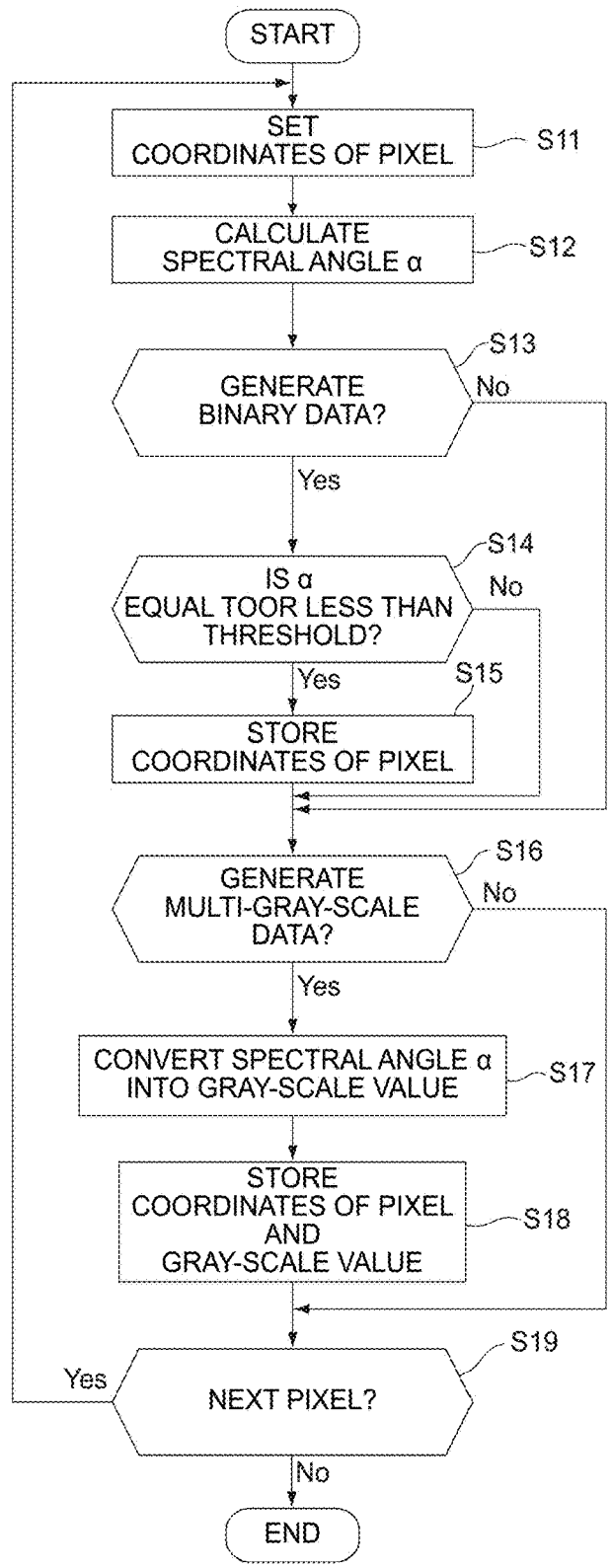
FIG. 6 is a flowchart showing an example of processing of comparing sample data with training data according to the present embodiment.

At Step S7 after the generation of the sample data is finished, the data generator 21 in the image analyzer 7 compares the sample data with the training data. FIG. 6 is a flowchart showing an example of processing of comparing the sample data with the training data using the spectral angle mapper classification. In the comparison processing, the data generator 21 sets a comparison target pixel in the sample data (Step S11). For example, comparison target pixels are selected in order from a pixel at the edge of the PiPk plane in the cube data shown in FIG. 2A.

At Step S12 in FIG. 6, the data generator 21 reads, from the STORAGE 15, pixel values of the comparison target pixels in the comparison data for the respective N wavelength bands. The data generator 21 reads, from the STORAGE 15, optical properties values of the training data for the respective N wavelength bands. The data generator 21 uses the read comparison data and the read training data to perform calculation in accordance with Expression (1) shown in FIG. 4B, thereby calculating a spectral angle $\alpha$ between the training data and the comparison data for the comparison target pixel.

In the present embodiment, the data generator 21 determines whether to generate data on a binary image (hereinafter referred to as binary data) (Step S13). For example, setting information indicating whether to generate binary data is stored in the STORAGE 15 shown in FIG. 1. The data generator 21 uses the setting information stored in the STORAGE 15 to make a determination at Step S13. For example, an instruction to generate binary data is defined in the setting information by default, but a user can change the settings so that binary data is not generated. Before the processing at Step S13 or in the processing at Step S13, the input device 6 shown in FIG. 1 receives an input of choosing whether to generate binary data. The data generator 21 may make a determination at Step S13 on the basis of this input.

When it is determined to generate binary data (Step S13; Yes), the data generator 21 extracts a pixel at which the spectral angle $\alpha$ is a threshold or less. At Step S14, the data generator 21 determines whether the spectral angle $\alpha$ is a threshold or less. When the spectral angle $\alpha$ is a threshold or less (Step S14; Yes), the data generator 21 stores coordinates of this comparison target pixel in the STORAGE 15 (Step S15). When it is determined at Step S13 not to generate binary data (Step S13; No) or when it is determined at Step S14 that the spectral angle $\alpha$ is less than a threshold (Step S14; No), the data generator 21 starts the processing at Step S16 to be described next.

In the present embodiment, the data generator 21 determines whether to generate data on a gray-scale image (Step S16). A gray-scale image is a multi-gray-scale image including three or more gray scales, and, for example, the gray-scale image is multicolored. The data on a gray-scale image is referred to as multi-gray-scale data as appropriate. For example, setting information indicating whether to generate multi-gray-scale data is stored in the STORAGE 15 shown in FIG. 1, and the data generator 21 uses the setting information stored in the STORAGE 15 to make a determination at Step S16. For example, an instruction to generate multi-gray-scale data is defined in the setting information by default, but a user can change the settings so that multi-gray-scale data is not generated. Before the processing at Step S16 or in the processing at Step S16, the input device 6 shown in FIG. 1 receives an input of choosing whether to generate multi-gray-scale data. The data generator 21 may make a determination at Step S16 on the basis of this input.

When it is determined to generate multi-gray-scale data (Step S16; Yes), the data generator 21 converts the spectral angle $\alpha$, which is the calculation result at Step S12, into a gray-scale value (Step S17). For example, the data generator 21 multiplies the spectral angle $\alpha$ by a conversion factor, and rounds the multiplied value to the nearest integer to calculate a gray-scale value corresponding to the spectral angle $\alpha$. In this case, the gray-scale value has a substantially linear relation to the spectral angle $\alpha$. The data generator 21 may convert the spectral angle $\alpha$ into a gray-scale value such that the spectral angle $\alpha$ and the gray-scale value have a non-linear relation. The data generator 21 stores the calculated gray-scale value in the STORAGE 15 in association with the coordinates of the comparison target pixel (Step S18).

When it is determined at Step S16 not to generate multi-gray-scale data (Step S16; No) or after the processing at Step S18, the data generator 21 determines whether to perform comparison processing for the next pixel (Step S19). When the next comparison target pixel is present (Step S19; Yes), the data generator 21 returns to Step S11 to set the next pixel as a comparison target pixel, and repeats the processing from Step S11 to Step S19. When the next comparison target pixel is absent (Step S19; No), the data generator 21 finishes the comparison processing.

By repeating the processing from Step S11 to Step S19, the data generator 21 performs the comparison processing at Step S7 in FIG. 5. The data generator 21 generates distribution data after the finish of the comparison processing (Step S8). When the settings are made such that binary data is generated, at Step S8, the data generator 21 reads the position of the pixel stored in the STORAGE 15 at Step S15 in FIG. 6. The data generator 21 generates data on a binary image as distribution data in a manner that the gray-scale value of a pixel at which the spectral angle $\alpha$ is a threshold or less is 0 and the gray-scale value of a pixel at which the spectral angle $\alpha$ is larger than a threshold is 255 (Step S9). When the settings are made such that multi-gray-scale data is generated, at Step S9, the data generator 21 reads the position of the pixel and its gray-scale value that are stored in the STORAGE 15 at Step S18 in FIG. 6, and arranges the gray-scale value in accordance with the position of the pixel, thereby generating data on a rule image.

Figure 7:
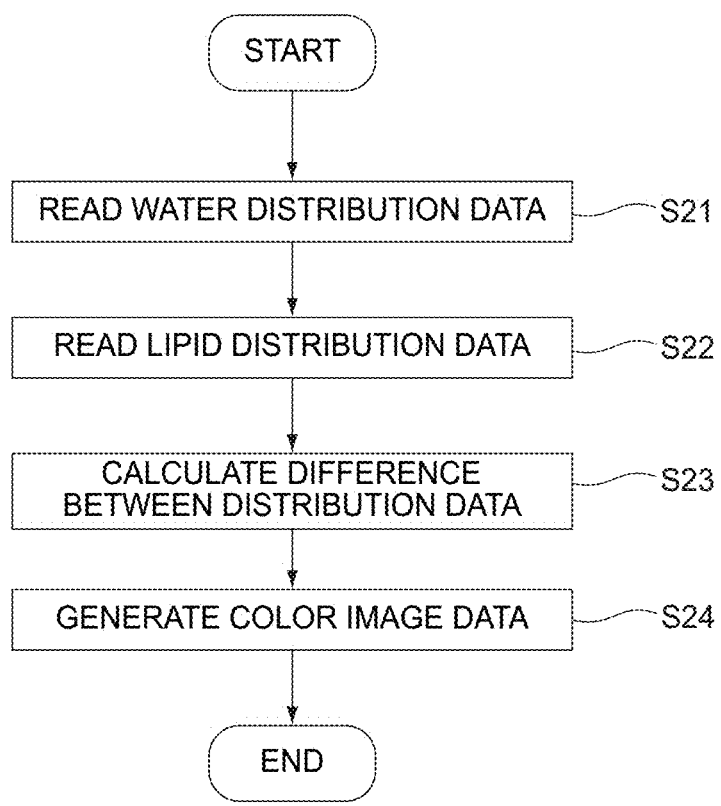
FIG. 7 is a flowchart showing an example of processing executed by a calculator according to the present embodiment.

The second calculator 22 performs calculation by using the distribution data generated by the data generator 21 in accordance with an instruction from an operator, for example. FIG. 7 is a flowchart showing an example of processing executed by the second calculator 22. At Step S21, the second calculator 22 reads water distribution data from the STORAGE 15. At Step S22, the second calculator 22 reads lipid distribution data from the STORAGE 15. The order of reading distribution data can be changed as appropriate, and the lipid distribution data may be read before the water distribution data. At Step S23, the second calculator 22 calculates the difference between the read water distribution data and the read lipid distribution data. At Step S24, the second calculator 22 generates color image data that indicates a differential image as a color image. For example, the second calculator 22 provides different colors for a part where the proportion of lipid is larger than the proportion of water and a part where the proportion of water is larger than the proportion of lipid.

Figure 8A:
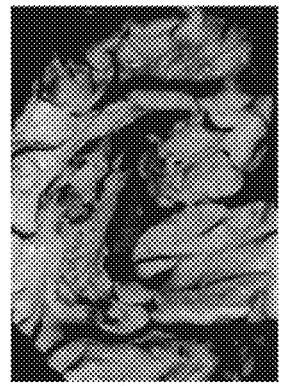
FIGS. 8A, 8B, 8C, 8D, 8E, 8F and 8G are each a diagram showing an example of images generated by an image analyzer according to the present embodiment.
Figure 8B:
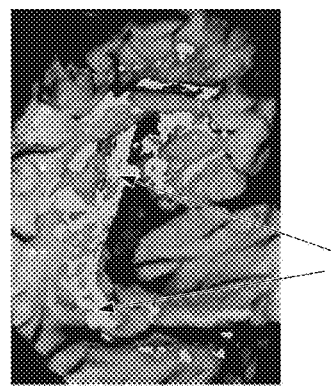
Figure 8C:
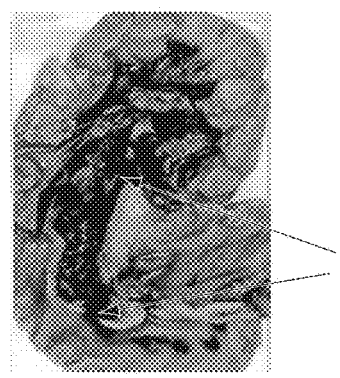
Figure 8D:
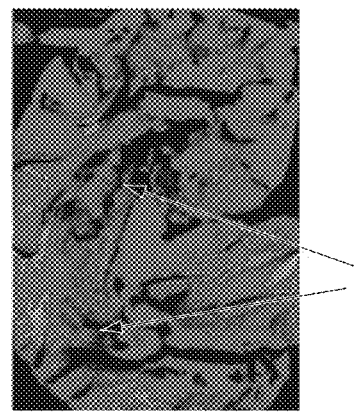
Figure 8E:
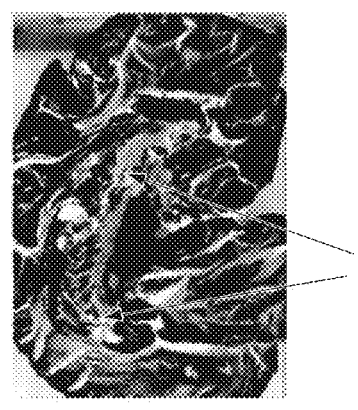
Figure 8F:
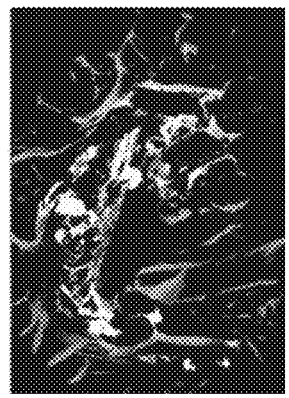
Figure 8G:

FIGS. 8A to 8G are each a diagram showing an example of images generated by the image analyzer 7 by using the above-described spectral angle mapper classification. FIG. 8A is an original image (sample image) of a tissue BT, and FIG. 8B is an image in which a binary image obtained when water is selected as a training substance is overlaid on the original image. In FIG. 8B, parts indicated by arrows are parts extracted by binarization, where the proportion of water is large. FIG. 8C is an image in which a rule image obtained when water is selected as a training substance is overlaid on the original image. In FIG. 8C, parts indicated by arrows are darker than those in the original image, which shows that the proportion of water is large. In FIG. 8C, the outside of the tissue BT is bright, which makes it easy to distinguish the tissue BT from the outside. FIG. 8D is an image in which a binary image obtained when lipid is selected as a training substance is overlaid on the original image. In FIG. 8D, parts indicated by arrows are parts extracted by binarization, where the proportion of lipid is large. FIG. 8E is an image in which a rule image obtained when lipid is selected as a training substance is overlaid on the original image. In FIG. 8E, parts indicated by arrows are darker than those in the original image, which shows that the proportion of lipid is large. Also in FIG. 8E, the tissue BT can be easily distinguished from the outside similarly to the water rule image. FIG. 8F is a differential image between the rule image obtained when water is selected as a training substance and the rule image obtained when lipid is selected as a training substance. In FIG. 8F, a part where the amount of water is larger is brighter, and a part where the amount of lipid is larger is darker. FIG. 8G is actually an image that indicates the differential image in FIG. 8F by color. The distribution of the training substances in these images satisfactorily matches with the results of pathological diagnosis, and it was confirmed by the image analyzer 7 that the distribution of the training substances was able to be accurately analyzed.

In the present embodiment, the control device 4 includes a computer including a CPU and a memory. In the control device 4, the computer executes various kinds of processing in accordance with an image analysis program. This program causes the computer to execute: generating, on the basis of a plurality of sample images for respective N wavelength bands selected from, for example, a wavelength bandwidth from 950 nm or more to 1600 nm or less as a predetermined wavelength bandwidth that are obtained by irradiating a biological tissue with light having the N wavelength bands, sample data including optical properties of the tissue in the predetermined wavelength bandwidth; and comparing the sample data with training data on a substance that is a training substance, to generate distribution data indicating a distribution of the substance in the tissue. This program may be stored in a computer-readable storage medium, such as an optical disc, a CD-ROM, a USB memory, or an SD card, and then provided.

As described above, the image analyzer 7 according to the present embodiment compares sample data including optical properties of a tissue BT in a wavelength bandwidth from 950 nm or more to 1600 nm or less with training data to generate distribution data on a training substance in the tissue BT. Consequently, the distribution of the training substance in the biological tissue BT can be accurately analyzed.

While similarity between sample data and training data is determined with use of the spectral angle α in the above description, the similarity may be determined with use of another index value. Next, a modification for determining similarity between sample data and training data by another algorithm will be described.

Figures 9, 10:
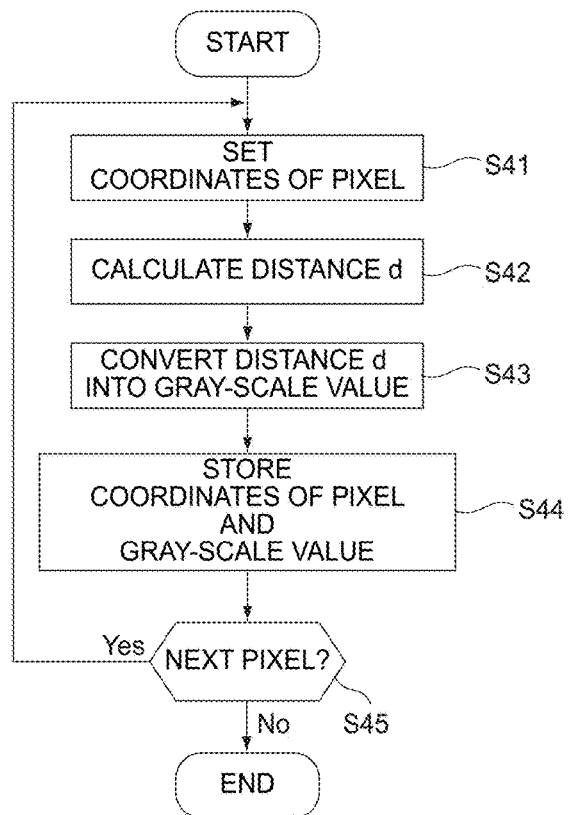
FIG. 9 is a flowchart showing an operation of an image analyzer according to a modification.
FIG. 10 shows an expression used for distance calculation according to the present embodiment.

FIG. 9 is a flowchart showing the operation of the image analyzer 7 according to the modification. FIG. 10 is a diagram showing Expression (2) used to calculate a distance d. Comparison processing executed by the data generator 21 in the image analyzer 7, which employs the minimum Euclidean distance classification, will be described. At Step S41, the data generator 21 sets a comparison target pixel to be compared with training data in comparison data. At Step S42, the data generator 21 reads comparison data for the comparison target pixel from the STORAGE 15, and calculates a distance d in accordance with Expression (2) shown in FIG. 10. In Expression (2), $x_{ik}$ is a pixel value in a k-th wavelength band in the comparison data. In other words, $x_{ik}$ corresponds to $t_{nb}$ in the vector Vt shown in FIG. 4A. $x_{jk}$ is an optical property value in the k-th wavelength band in the training data. In other words, $x_{jk}$ corresponds to $r_{nb}$ in the vector Vr shown in FIG. 4A. p is the number of wavelength bands, and corresponds to nb in FIG. 4A. The sample data becomes more similar to the training data as the distance d calculated by Expression (2) becomes smaller.

At Step S43, the data generator 21 converts the distance d calculated at Step S42 into a gray-scale value. For example, the data generator 21 multiplies the distance d by a conversion constant, and rounds the multiplied value to calculate a gray-scale value. At Step S44, the data generator 21 stores the gray-scale value calculated at Step S43 and the coordinates of the comparison target pixel in the STORAGE 15 in association with each other. At Step S45, the data generator 21 determines whether the next comparison target pixel is present. When it is determined at Step S45 that the next comparison target pixel is present (Step S45; Yes), the data generator 21 returns to Step S41 to repeat the processing until Step S46. When it is determined at Step S45 that the next comparison target pixel is absent (Step S45; No), the data generator 21 finishes the comparison processing.

Figure 11A:
FIGS. 11A, 11B, 11C, 11D, and 11E are each a diagram showing an example of images generated by an image analyzer according to the modification.
Figure 11B:
Figure 11C:
Figure 11D:
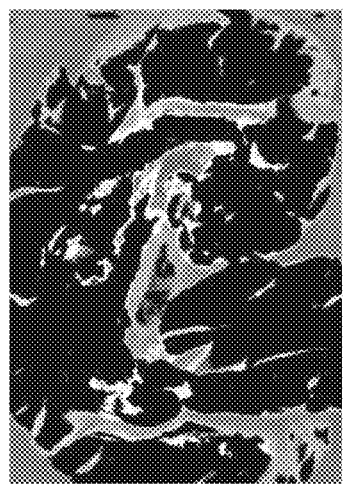
Figure 11E:
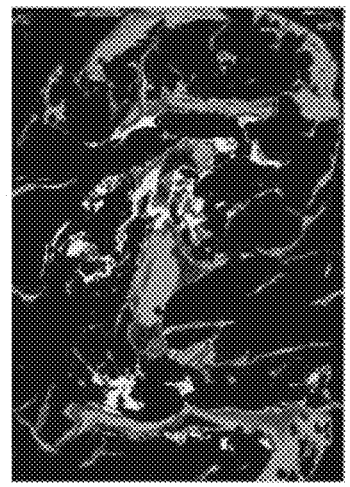

FIGS. 11A to 11E are each a diagram showing an example of images generated by the image analyzer 7 according to the present modification. FIG. 11A is an original image of a tissue BT, which is the same as FIG. 8A. FIG. 11B is an image in which a rule image obtained when water is selected as a training substance is overlaid on the original image. FIG. 11C is an image in which a rule image obtained when lipid is selected as a training substance is overlaid on the original image. FIG. 11D is a differential image between the rule image obtained when water is selected as a training substance and the rule image obtained when lipid is selected as a training substance. FIG. 11E is actually an image that indicates the differential image in FIG. 11D by color. It was confirmed by the image analyzer 7 that the distribution of the training substances was able to be accurately analyzed by images.

The image analyzer 7 according to the present modification compares sample data including optical properties of a tissue BT in a wavelength bandwidth from 950 nm or more to 1600 nm or less with training data to generate distribution data on training substances in the tissue BT. Consequently, the distribution of the training substances in the biological tissue BT can be accurately analyzed.

While in the present embodiment, the image analysis apparatus is the image analyzer 7 embedded in the control device 4, the image analysis apparatus may be an apparatus different from the control device. The image analyzer 7 may generate distribution data by using sample data acquired by an apparatus different from the imaging apparatus 3.

When the number of pixels arranged in the Y-axis direction in the light detector 12 is L, the light detector 12 can detect light radiated from the tissue BT separately for L wavelength bands. The image analyzer 7 only needs to use detection results for at least two training substances among detection results for the L wavelength bands, and does not need to use detection results for one or more wavelength bands. By using an average value of detection results by two or more pixels arranged in the Y-axis direction in the light detector 12, the light intensity in a wavelength band of light entering the two or more pixels may be used for image analysis.

While the imaging apparatus 3 detects light reflected and scattered by the tissue BT in the present embodiment, the imaging apparatus 3 may detect light transmitted through the tissue BT and radiated from the tissue BT. In this case, sample data is a value corresponding to the transmittance (optical property value) of the tissue BT. Thus, it is preferred to use data related to the transmittance of a training substance as training data. For example, the imaging apparatus 3 may be used to detect light transmitted through and radiated from a training substance, and the detection result may be used to generate training data.

Figure 12A:
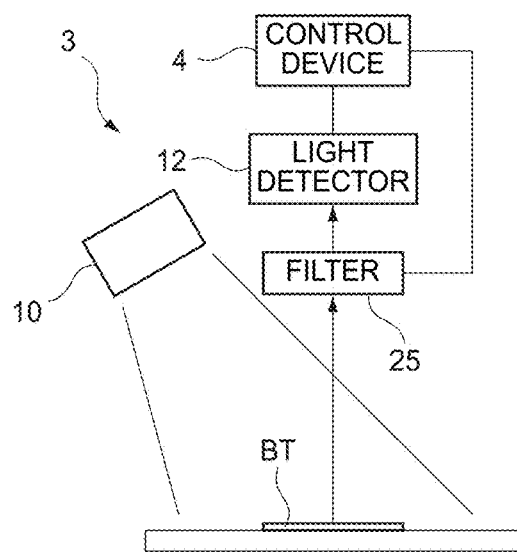
FIGS. 12A and 12B are each a diagram showing other configurations of an imaging apparatus according to the present embodiment.
Figure 12B:
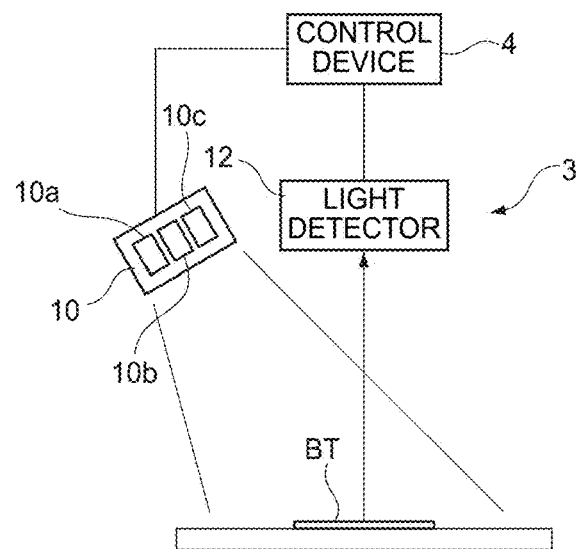

While in the present embodiment, the imaging apparatus 3 disperses light radiated from the tissue BT to acquire a hyperspectral image, the imaging apparatus 3 may employ another configuration. For example, the imaging apparatus 3 may be configured to acquire data (for example, sample data or training data) while switching the wavelength bandwidth of light output from the light source. Examples of the method of acquiring a hyperspectral image in the present embodiment include spatial scanning, spectrum scanning, Fourier transform, and interference filtering. FIG. 12A and FIG. 12B are each a diagram showing another configuration of the imaging apparatus 3. The control device 4 has the same configuration as in the above, and the image analyzer 7 can generate distribution data by using the above-described comparison processing based on obtained sample images.

The imaging apparatus 3 shown in FIG. 12A includes a light source 10, a filter 25, and a light detector 12. The light source 10 outputs infrared light across a wide wavelength bandwidth corresponding to a predetermined wavelength bandwidth. The filter 25 is disposed in an optical path between the light source 10 and the light detector 12. For example, the filter 25 is provided in at least one of an optical path between the light source 10 and the tissue BT and an optical path between the tissue BT and the light detector 12. The filter 25 includes a plurality of filters, and the plurality of filters transmit infrared light having different wavelengths. The filter 25 is driven by a driver (not shown), and can switch a filter disposed between the light source 10 and the light detector 12 among the plurality of filters.

The control device 4 controls a driver for the filter 25 to switch a filter disposed in an optical path between the light source 10 and the light detector 12, thereby controlling the wavelength of infrared light entering the light detector 12. For example, the control device 4 disposes a first filter that transmits infrared light having a first wavelength band in the optical path between the light source 10 and the light detector 12. The control device 4 controls the light detector 12 to capture an image of the tissue BT in a period during which the infrared light having the first wavelength band radiated from the tissue BT enters the light detector. The control device 4 acquires a spatial distribution of light intensity of the infrared light having the first wavelength band radiated from the tissue BT on the basis of the capture result of the light detector 12. Similarly, the control device 4 disposes a first filter that transmits infrared light having a second wavelength band in the optical path between the light source 10 and the light detector 12, and a spatial distribution of light intensity of the infrared light having the first wavelength band radiated from the tissue BT. In this manner, the control device 4 is capable of generating sample data in N wavelength bands.

The imaging apparatus 3 shown in FIG. 12B includes a light source 10 and a light detector 12. The light source 10 includes a light source 10a that outputs infrared light having a first wavelength band, a light source 10b that outputs infrared light having a second wavelength band, and a light source 10c that outputs infrared light having a third wavelength band. The control device 4 controls turning-on and turning-off of each of the light source 10a, the light source 10b, and the light source 10c. The control device 4 turns on the light source 10a and turns off the light source 10b and the light source 10c. In this manner, infrared light having the first wavelength band is output from the light source 10, and infrared light having the first wavelength band radiated from the tissue BT enters the light detector 12. The control device 4 controls the light detector 12 to capture an image while switching a turned-on light source among the light source 10a, the light source 10b, and the light source 10c. In this manner, the control device 4 can generate sample data in the N wavelength bands.

While the imaging system 1 according to the present embodiment generates training data by using the imaging apparatus 3, the imaging system 1 does not have to generate training data by using the imaging apparatus 3. For example, training data may be generated in advance and stored in the STORAGE 15, and the data generator 21 may read the training data from the STORAGE 15 to generate distribution data. The training data stored in the STORAGE 15 may be generated by using the imaging apparatus 3 or may be generated by using an apparatus other than the imaging apparatus 3. The training data may be obtained by storing available one of data written in a book, data recorded in a recording medium, and data stored in an external database in the STORAGE 15.

In the present embodiment, N in the N wavelength bands is an integer of 2 or more and M in the M wavelength bands is an integer of 2 or more, and then N and M are equal numbers (N=M). If training data is given in advance, however, M and N may be different. Furthermore, wavelength bands included in training data and wavelength bands included in sample data may be mismatched from each other. For example, an optical property value in the first wavelength band may be present in one of training data and sample data, and the optical properties value in the first wavelength band may be absent in the other data. In such a case where one of the paired data is lacked, the data generator 21 can calculate the missing data. The data generator 21 can calculate an index value (degree of similarity, spectral angle) indicating similarity in a manner that data in the first wavelength band is excluded. In this manner, the data generator 21 matches the dimension of the sample data with the dimension of the training data to calculate an index value indicating similarity.

While the stage device 2 moves in the Y-axis direction in the present embodiment, the stage device 2 may move in at least one of the X-axis direction or the Z-axis direction (for example, X-axis direction). The stage device 2 may be rotatable in at least one of a direction about the X axis, a direction about the Y axis, or a direction about the Z axis. While in the present embodiment, the tissue BT is scanned with infrared light from the light source 10 along with the movement of the stage device 2, the tissue BT may be scanned with the infrared light along with the movement of the light source 10. The imaging system 1 does not have to include the stage device 2.

Figure 13:
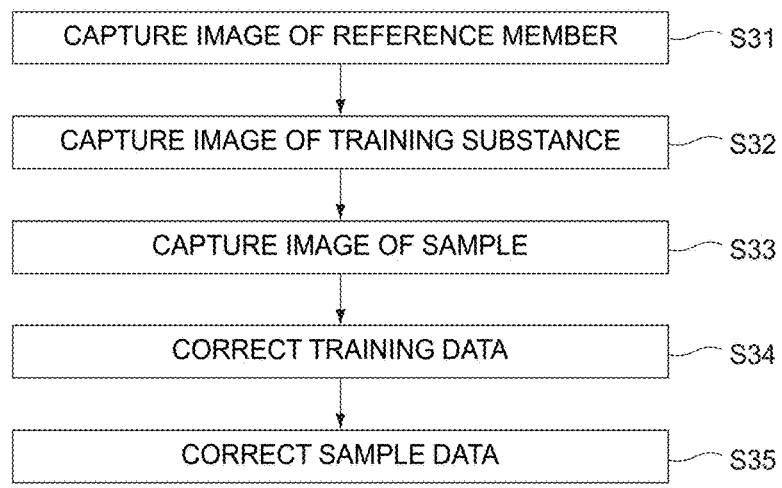
FIG. 13 is a flowchart showing an example of correction according to the present embodiment.

While in the present embodiment, the image analyzer 7 generates distribution data by directly using data (raw data) on an image captured by the imaging apparatus 3, the image analyzer 7 may generate distribution data by using corrected captured image data. FIG. 13 is a flowchart showing an example of correction according to the present embodiment. In this case, the light intensity of light reflected by the surface of a reference member (reference) such as a white plate is used to normalize (standardize) the light intensity of light reflected by the surface of a sample (for example, a tissue, a training substance).

At Step S31 in FIG. 13, the control device 4 controls the light source 10 to irradiate the reference member with infrared light having a predetermined wavelength bandwidth. The control device 4 controls the imaging apparatus 3 to capture an image of the reference member irradiated with the infrared light while moving the stage device 2 relative to the light source 10. Next, at Step S32, the control device 4 controls the light source 10 to irradiate a training substance with infrared light having a predetermined wavelength bandwidth (for example, the same bandwidth as the wavelength bandwidth of the light applied to the reference member), and controls the imaging apparatus 3 to capture an image of the reference member while moving the stage device 2 relative to the light source 10. Next, at Step S33, the control device 4 controls the light source 10 to irradiate a sample with infrared light having a predetermined wavelength bandwidth, and controls the imaging apparatus 3 to capture an image of the sample while moving the stage device 2 relative to the light source 10. The order of the processing from Step S31 to Step S33 can be changed as appropriate.

After the finish of the processing at Step S31 and the processing at Step S32, the control device 4 uses the capture result of the reference member to normalize the capture result of the sample image (Step S34). The light intensity of light that is radiated from the reference member for each wavelength $\lambda$ in the predetermined wavelength bandwidth is represented by $I_0(\lambda)$, and the light intensity of light radiated from the training substance for each wavelength $\lambda$ in the predetermined wavelength bandwidth is represented by $I_1(\lambda)$. The control device 4 calculates the value $(I_1(\lambda)/I_0(\lambda))$ obtained by dividing $I_1(\lambda)$ by $I_0(\lambda)$ as a first corrected value $R_1(\lambda)$.

After the finish of the processing at Step S31 and the processing at Step S33, the control device 4 uses the capture result of the reference member to normalize the capture result of the sample (Step S35). The light intensity of light that is radiated from the sample for each wavelength $\lambda$ in the predetermined wavelength bandwidth is represented by $I_2(\lambda)$. The control device 4 calculates the value $(I_2(\lambda)/I_0(\lambda))$ obtained by dividing $I_2(\lambda)$ by $I_0(\lambda)$ as a second corrected value $R_2(\lambda)$.

The image analyzer 7 uses the first corrected value $R_1(\lambda)$ as corrected training data and uses the second corrected value $R_2(\lambda)$ as corrected sample data to generate distribution data as shown in FIG. 5. The order of the processing at Step S34 and the processing at Step S35 can be changed as appropriate, and the processing at Step S35 may be performed before the processing at Step S34. At least a part of the correction processing may be performed by the image analyzer 7 or by another calculator.

[Surgery Support System]

Figure 14:
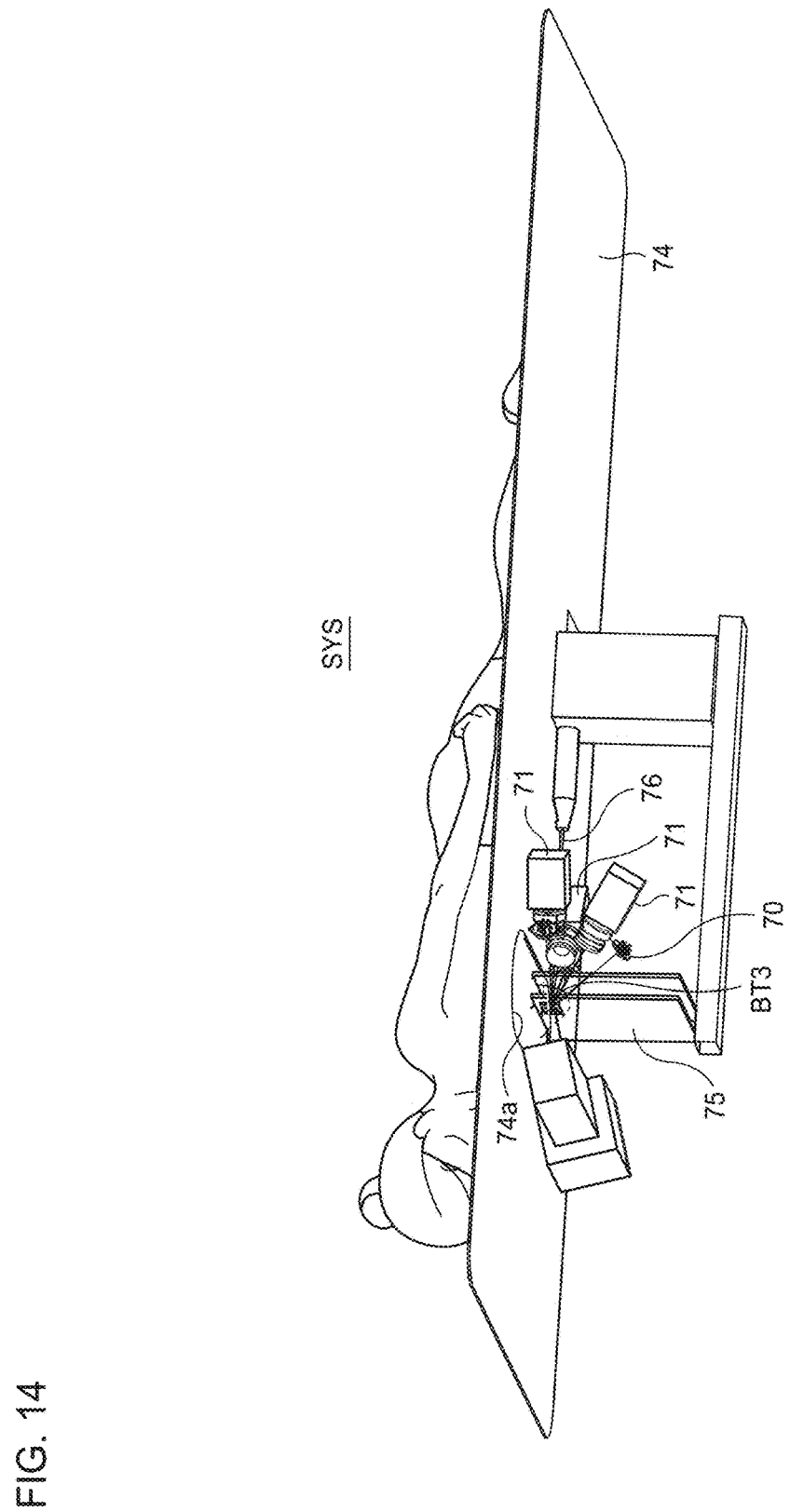
FIG. 14 is a diagram showing a surgery support system to which an image analysis apparatus according to the present embodiment is applied.

Next, a surgery support system (medical support system) will be described. FIG. 14 is a diagram showing an example of a surgery support system SYS. The surgery support system SYS is a mammotome using the image analyzer 7 described in the above-described embodiment. The surgery support system SYS includes a lighting device 70 and an infrared camera 71. The lighting device 70 is an irradiator that irradiates a tissue such as a breast with detection light. The infrared camera 71 is a light detector that detects light radiated from the tissue. The image analyzer (image analysis apparatus) generates sample data on the basis of the detection result of the infrared camera 71, and compares the sample data with training data to generate distribution data on a training substance.

The surgery support system SYS also includes a bed 74, a transparent plastic plate 75, and a perforation needle 76. The bed 74 is a bed on which an examinee lies with his or her face down. The bed 74 has an aperture 52a through which a breast BT3 (tissue) of the examinee as the subject is exposed downward. The transparent plastic plate 75 is used to sandwich both sides of the breast BT3 to flatten the breast BT3. The perforation needle 76 is an operation device capable of treating the tissue. The perforation needle 76 is inserted into the breast BT3 in a core needle biopsy to take a sample.

As shown in FIG. 14, the breast BT3 is flattened by pressing the transparent plastic plate 75 against both sides thereof, and in this state, the lighting device 70 outputs infrared light having a predetermined wavelength band so that the infrared camera 71 captures an image. In this manner, the infrared camera 71 acquires an image of the breast BT3 with infrared light reflected from the lighting device 70.

In a general core needle biopsy, a perforation needle (core needle) is inserted while measuring the depth of the needle using ultrasonic echo. A breast generally includes tissues with a large amount of lipid, but when a breast cancer occurs, the amount of water in the breast cancer area may differ from that in other areas.

The surgery support system SYS can insert the perforation needle 76 into the breast BT3 to take a tissue while displaying a distribution of a training substance in the breast BT3 generated by the image analysis apparatus in the present embodiment. For example, an operator can insert the perforation needle 76 into a part of the breast BT3 where the amount of water is different from those in other parts while observing a distribution image generated by the image analysis apparatus. Such a surgery support system SYS can take a sample while accurately analyzing the distribution of the training substance in the tissue. Imaging with infrared light, which does not cause X-ray exposure, can be usually used in obstetrics and gynecology, regardless of whether the patient is pregnant. In this manner, for example, the surgery support system SYS includes the imaging system 1 including the image analyzer 7, and an operation device such as the perforation needle 76.

Next, another example of the surgery support system SYS will be described. Another surgery support system SYS in the present embodiment is used for laparotomy or other operations. The surgery support system SYS includes the above-described imaging system 1 in the present embodiment, and an operation device (not shown) capable of treating a tissue ET to be treated in the state in which an image about the tissue BT, which is obtained by the imaging system 1 (or the image analyzer 7), is displayed on a display. For example, the operation device includes at least one of a blood sampling device, a hemostatic device, a laparoscopic device including endoscopic instruments, an incisional device, or an abdominal device. The invasiveness and efficiency of surgical therapy are determined by the range and intensity of damage and cauterization associated with incision and hemostasis. The surgery support system SYS displays an image indicating information on tissues on the display, and hence an affected area, such as a cancer, as well as organs, such as nerves and pancreas, and lipid tissues can be easily visually recognized to reduce the invasiveness of surgical therapy and enhance the efficiency of surgical therapy.

The technical scope of the present invention is not limited to the above-described embodiments or modifications. For example, one or more elements described in the above-described embodiments or modifications may be omitted. The elements described in the above-described embodiments or modifications can be combined as appropriate.

DESCRIPTION OF REFERENCE SIGNS

1 . . . imaging system, 3 . . . imaging apparatus, 7 . . . image analyzer, 20 . . . calculator, 21 . . . data generator, 22 . . . second calculator

What is claimed is:

1. An imaging system comprising:
an imaging device that acquires a hyperspectral image obtained by irradiating a biological tissue with infrared light having a predetermined wavelength band;
a calculator that generates, on the basis of the hyperspectral image, sample data on the tissue in the predetermined wavelength band; and
a data generator that compares the sample data with training data on water that is a training target, to generate first image data indicating a distribution of the water in the tissue, and compares the sample data with training data on lipid that is a training target, to generate second image data indicating a distribution of the lipid in the tissue.

2. The imaging system of claim 1, wherein the data generator performs processing of combining a sample image based on the sample data with a water rule image based on the training data on the water to generate the first image data.

3. The imaging system of claim 2, wherein the data generator performs processing of combining a sample image based on the sample data with a lipid rule image based on the training data on the lipid to generate the second image data.

4. The imaging system of claim 3, wherein the data generator generates, on the basis of the first image data or the second image data, a color image indicating a distribution of the water or a distribution of the lipid.

5. The imaging system of claim 1, wherein the data generator compares the sample data with training data on a protein that is a training target, to generate third image data indicating a distribution of the protein in the tissue.

6. A surgery support system comprising:
the imaging system of claim 1; and
a display that displays an image based on the first image data or an image based on the second image data.

7. An imaging method comprising:
acquiring a hyperspectral image obtained by irradiating a biological tissue with infrared light having a predetermined wavelength band;
generating, on the basis of the hyperspectral image, sample data on the tissue in the predetermined wavelength band; and
comparing the sample data with training data on water that is a training target, to generate first image data indicating a distribution of the water in the tissue, and comparing the sample data with training data on lipid that is a training target, to generate second image data indicating a distribution of the lipid in the tissue.

8. A non-transitory storage medium that stores therein an image analysis program that causes a computer to execute:
acquiring a hyperspectral image obtained by irradiating a biological tissue with infrared light having a predetermined wavelength band;
generating, on the basis of the hyperspectral image, sample data on the tissue in the predetermined wavelength band; and
comparing the sample data with training data on water that is a training target, to generate first image data indicating a distribution of the water in the tissue, and comparing the sample data with training data on lipid that is a training target, to generate second image data indicating a distribution of the lipid in the tissue.

9. An image analysis apparatus comprising:
a calculator that generates, on the basis of a plurality of pieces of sample information obtained by irradiating a biological tissue with infrared light having N wavelength bands selected from a predetermined wavelength bandwidth, sample data on the tissue in the predetermined wavelength bandwidth; and
a data generator that compares the sample data with training data on water that is a training target, with use of at least one of spectral angle mapper classification, spectral correlation mapper classification, or Euclidean distance classification, to generate distribution data indicating a distribution of the water in the tissue, wherein
the predetermined wavelength bandwidth is set from a wavelength bandwidth from 700 nm or more to 2500 nm or less as a training region for the water.

10. The image analysis apparatus of claim 9, wherein the data generator compares the sample data with training data on lipid that is a training target, with use of at least one of spectral angle mapper classification, spectral correlation mapper classification, or Euclidean distance classification, to generate distribution data indicating a distribution of the lipid in the tissue.

11. The image analysis apparatus of claim 9, wherein the data generator compares the sample data with training data on blood that is a training target, with use of at least one of spectral angle mapper classification, spectral correlation mapper classification, or Euclidean distance classification, to generate distribution data indicating a distribution of the blood in the tissue.

12. An imaging system comprising:
an imaging device that acquires a hyperspectral image obtained by irradiating a biological tissue with infrared light having a predetermined wavelength band;
a calculator that generates, on the basis of the hyperspectral image, sample data on the tissue in the predetermined wavelength band; and
a data generator that compares the sample data with training data on water that is a training target, with use of at least one of spectral angle mapper classification, spectral correlation mapper classification, or Euclidean distance classification, to generate first image data indicating a distribution of the water in the tissue, wherein
the predetermined wavelength bandwidth is set from a wavelength bandwidth from 700 nm or more to 2500 nm or less as a training region for the water.

13. The imaging system according to claim 12, comprising:
an input device that accepts input from a user.

14. The imaging system according to claim 12, comprising:
- a light source that outputs infrared light having a spot shape elongated in one direction.

15. The imaging system according to claim 12, wherein the data generator compares the sample data with training data on lipid that is a training target, with use of at least one of spectral angle mapper classification, spectral correlation mapper classification, or Euclidean distance classification, to generate second image data indicating a distribution of the lipid in the tissue.

16. The imaging system according to claim 12, wherein the data generator compares the sample data with training data on blood that is a training target, with use of at least one of spectral angle mapper classification, spectral correlation mapper classification, or Euclidean distance classification, to generate third image data indicating a distribution of the blood in the tissue.

* * * * *